United States Patent
Askill et al.

[11] Patent Number: 5,730,994
[45] Date of Patent: Mar. 24, 1998

[54] METHODS FOR DRAPING SURGICAL INCISION SITES

[75] Inventors: Ian N. Askill, Colorado Springs, Colo.; Richard J. Greff, St. Pete Beach, Fla.; Michael M. Byram, Colorado Springs, Colo.; Richard T. VanRyne, Lake Forest, Calif.

[73] Assignee: MedLogic Global Corporation, Colorado Springs, Colo.

[21] Appl. No.: 781,279

[22] Filed: Jan. 10, 1997

[51] Int. Cl.$^6$ ..................................... A01N 25/34
[52] U.S. Cl. .................. 424/402; 424/78.35; 523/105; 523/111
[58] Field of Search .................... 424/402, 78.35; 523/105, 111

[56] References Cited

U.S. PATENT DOCUMENTS

| | | |
|---|---|---|
| 4,374,126 | 2/1983 | Cardarelli et al. . |
| 4,542,012 | 9/1985 | Dell . |
| 4,646,765 | 3/1987 | Cooper et al. .......... 523/105 |
| 4,713,235 | 12/1987 | Krall . |
| 4,978,527 | 12/1990 | Brink et al. . |
| 4,994,542 | 2/1991 | Matsuda et al. . |
| 5,051,256 | 9/1991 | Barnes .................. 424/402 |
| 5,069,907 | 12/1991 | Mixon et al. ............ 424/402 |
| 5,236,703 | 8/1993 | Usala .................... 424/402 |
| 5,306,490 | 4/1994 | Barley, Jr. ............. 523/111 |
| 5,328,687 | 7/1994 | Leung et al. . |
| 5,457,141 | 10/1995 | Matsuda et al. ......... 523/111 |
| 5,480,935 | 1/1996 | Greff et al. . |
| 5,530,037 | 6/1996 | McDonnell et al. ...... 523/111 |
| 5,547,662 | 8/1996 | Khan et al. . |

FOREIGN PATENT DOCUMENTS

WO 96/23532  8/1996  WIPO .

OTHER PUBLICATIONS

Ritter, M.A., et al., "Retrospective Evaluation of an iodophor-Incorporated Antimicrobial Plastic Adhesive Wound Drape"—Clinical Orthopedics and Related Research, (1986) pp. 307–308.

Sidorva, et al., Prevention of Incompetence of a Uterine Suture Following Ceasarian Section, Akusherstvo I. Ginekoogiia, (Mar. 1989) 3:30–33.

Timokhina, V.I., "Biological Properties of New Cement Compositions For Medical Use", Biodestruktiruysshchve Polim. Mater. (1982) 55–61.

Primary Examiner—Joseph L. Schofer
Assistant Examiner—N. Sarofin
Attorney, Agent, or Firm—Burns, Doane, Swecker & Mathis, L.L.P.

[57] ABSTRACT

Disclosed are methods for draping a surgical incision site prior to surgery. Specifically, the methods of this invention involve the in situ formation of a cyanoacrylate polymeric drape over the skin surface at the surgical incision site. An incision is then made through this surface and the surgery is then conducted through the incision.

14 Claims, No Drawings

METHODS FOR DRAPING SURGICAL INCISION SITES

BACKGROUND OF THE INVENTION

Field of the Invention

This invention is directed to methods for draping a surgical incision site prior to surgery. Specifically, the methods of this invention involve the in situ formation of a polymeric cyanoacrylate drape over the skin surface at the surgical incision site. An incision is made through the drape and surgery is then conducted through the incision.

References

The following publications, patent applications and patents are cited in this application as superscript numbers:

1. Masterson, M. D., "Skin Preparation", Chapter 9, in *Surgical Infections, Diagnosis and Treatment*, Meakins, Ed., Scientific American, Inc., New York, USA, Publisher, pp. 119–125 (1994)
2. Osuna, et al., "Comparison of an Antimicrobial Adhesive Drape and Povidone-Iodine Preoperative Skin Preparation in Dogs", Veterinary Surgery, 21(6):458–462 (1992)
3. Hagen, et al., "A Comparison of Two Skin Preps Used in Cardiac Surgical Procedures", AORN Journal, 62(3):393–402 (1995)
4. Alexander, et al., "Development of a Safe and Effective One-Minute Preoperative Skin Preparation", Arch. Surg., 120:1357–1361 (1985)
5. Chiu, et al., "Plastic Adhesive Drapes and Wound Infection After Hip Fracture Surgery", Aust. N. Z. J. Surg., 63:798–801 (1993)
6. Barley, "Methods for Retarding Blister Formation by Use of Cyanoacrylate Adhesives", U.S. Pat. No. 5,306,490, issued Apr. 26, 1994.
7. Barley, et al., *Methods for Treating Suturable Wounds by Use of Sutures and Cyanoacrylate Adhesives*, U.S. Pat. No. 5,254,132, issued Oct. 19, 1993
8. McIntire, et al., U.S. Pat. No. 3,654,239, for *Process for the Preparation of Poly(α-Cyanoacrylates)*, issued Apr. 4, 1972
9. Barley, et al., International Patent Application Publication No. WO 93/25196, for *Methods for Treating Non-Suturable Wounds by Use of Cyanoacrylate Adhesives*, published Dec. 23, 1993
10. Barley, et al., U.S. Pat. No. 5,653,789, for *Methods for Reducing Skin Irritation From Artificial Devices by Use of Cyanoacrylate Adhesives*, filed Feb. 24, 1994
11. Tighe, et al., U.S. Pat. No. 5,403,591, for *Methods for Inhibiting Skin Ulceration by Use of Cyanoacrylate Adhesives* issued Apr. 4, 1995
12. Tighe, et al., U.S. Pat. No. 5,580,565, for *Use of Cyanoacrylates for Providing a Protective Barrier*, filed Sep. 1, 1994.
13. Ritter, et al., "Retrospective Evaluation of an Iodophor-Incorporated Antimicrobial Plastic Adhesive Wound Drape", Clinical Orthopedics and Related Research, pp. 307–308 (1988)
14. Duhaime, et al., "Distribution of Bacteria in the Operating Room Environment and its Relation to Ventricular Shunt Infections: a Prospective Study", Child's Very. Syst., 7:211–214 (1991)
15. O'Sullivan, et al., U.S. Pat. No. 4,038,345, for *High Viscosity Cyanoacrylate Adhesive Compositions, and Process for Their Preparation*, issued Jul. 26, 1977

All of the above publications, patent applications and patents are herein incorporated by reference in their entirety to the same extent as if each individual publication, patent application or patent was specifically and individually indicated to be incorporated by reference in its entirety.

State of the Art

Reduced morbidity and/or infection associated with surgical procedures necessitates the thorough preparation of the patient's skin prior to initiating any incision into the skin as part of the surgical procedure. The sole reason for patient skin preparation is to reduce the risk of wound infection by introduction of microbes into the incision site[1] from either endogenous sources or from air borne microbes.[4] In turn, reduction in such risk correlates, obviously, with reductions in the population of microbes on the skin surface and especially at the skin surface adjacent to the incision site.

Suitable skin preparation involves, for example, application of an antimicrobial agent onto and around the skin surface adjacent to the incision site which reduces the population of microbes on these surfaces and, hence the relative risk of infection. However, the skin is never completely sterilized during these procedures and microbes from hair follicles and sweat/sebaceous glands will migrate to the surface of the skin thereby raising microbial populations and accordingly relative infection risks.[2] To counter possible microbial migration into the incision, it has become common practice to employ a surgical incise drape over the patient's incision site.

Conventional surgical incise drapes include those which comprise a polymeric film coated with a pressure-sensitive adhesive. In some cases, an antimicrobial agent is incorporated directly into the adhesive in order to permit a continuous release of the antimicrobial agent onto the skin.[3,13] After application of an antimicrobial agent onto the skin surface of the patient, the surgical incise drape is applied, adhesive side down, with pressure to effect adherence of the drape to the skin. A surgical incision is then made through the drape and the requisite surgery is conducted through this incision. After completion of the surgery, the drape is conventionally removed from the skin surface.

Notwithstanding the benefits associated with a surgical incise drape, several problems exist which have both limited the general applicability of these drapes to all surgical incisions and have actually increased the relative risk of infection. Specifically, the first most common and potentially serious problem associated with the use of conventional surgical incise drapes is the separation or lifting of the drape from the skin surface during surgery. In one study, it was reported that up to 44% of the drapes experienced lifting during human surgery[2]. In turn, Alexander, et al.[4] report a sixfold increase in infections rates in operations in which the surgical incise drape lifted away from the skin during surgery as compared to infection rates in which the drape did not separate from the skin. Without being limited by any theory, it is generally believed that occlusion of the skin by the surgical incise drape provides a moist, warm skin surface which encourages microbial growth. It is further believed that lifting of the drape from the skin during surgery permits migration of microbes and/or microbial growth at these sites and, accordingly, in such cases, the use of a drape actually promotes rather than retards microbial populations at the incision site.

Non-adherence of the surgical incise drape to the patient's skin is, of course, related to adhesive failure as well as wrinkling of the polymeric film during application. In the former case, this has lead to some attempts to increase the amount and/or strength of adhesive employed in the drape.

However, this in turn may lead to more rather than fewer complications. In particular, since the drape is conventionally removed from the skin after surgery, an increase in the relative strength of the adhesive leads to increased difficulty in removing the drape from the skin. The effort required to effect removal can also lead to skin tearing, especially adjacent to the incision site, as well as removal of hair. Skin tearing is clearly disadvantageous and invariably raises additional infection risks whereas removal of hair (e.g., shaving) has also been associated with increased infection rates[2].

In the latter case, wrinkling of the polymeric drape is essentially irreversible because the wrinkles cannot be smoothed out absent complete removal of the drape. Additionally, air pockets in the wrinkles are undesireable because they provide a source of microbes adjacent to the skin and, in some cases, promote microbial growth. Wrinkling of the polymeric film is common to all applications of the surgical incise drapes but is particularly problematic with contoured surfaces such as elbows, knees, bony hips, etc. This, in turn, has limited the use of such conventional drapes.

An additional problem associated with polymeric films used as surgical incision drapes arises because such drapes do not conform well to three dimensional contours of the human body thereby increasing the likelihood of lifting during surgery. For example, while abdominal surfaces typically are flat and therefore good candidates for surgical incise drapes, other surfaces such as elbow, knee, foot, and bony hip surfaces (as examples) have three dimensional contours which render consistent adherence of the drape over the incision site during surgery problematic at best. In this regard, Chiu, et al.[5] report that the use of sterile adhesive drapes during hip fracture surgeries did not affect the post-operative wound infection rate but appeared to have actually encouraged microbial accumulation in the skin adjacent to the wound.

Still a further problem arises from the fact that the adhesive employed with the polymeric film does not adhere well to hair thereby limiting their utility[2]. Additionally, as noted above, shaving to remove hair prior to surgery has been clinically associated with increased wound infection rates.[1]

Lastly, while the most important purpose of using surgical incise drapes is to prevent postoperative wound infections, the simple fact of the matter is that the drape is removed after surgery and there is, accordingly, no postoperative antimicrobial effect available to the skin surface at the surgical incision site.

This invention is directed, in part, to the discovery that the in situ formation of a cyanoacrylate polymeric drape at the surgical incision site prior to surgery overcomes many of the prior art problems associated with the use of conventional surgical incise drapes and additionally provides incremental advantages heretofore not achieved by conventional drapes.

The use of cyanoacrylate polymers per this invention is in contrast to their known medical uses as an alternative or adjunct to sutures[7] or as a hemostat[8]. Other described uses of cyanoacrylate polymers include their use to prevent friction blister formation[6], treating small non-suturable wounds[9], and in inhibiting surface skin irritation arising from friction between the skin surface and artificial devices such as tapes, prosthetic devices, casts, and the like.[10]

SUMMARY OF THE INVENTION

This invention is directed to methods for draping a surgical incision site by application of a cyanoacrylate composition to the surface of the surgical incision site.

In situ polymerization of the cyanoacrylate composition provides for an adherent polymeric film over the surgical incision site which acts as a surgical incise drape during subsequent surgery. The adherence of the polymeric film to the skin surface is so strong that the possibility of lifting of the drape during surgery is effectively removed. Additionally, the cyanoacrylate composition can be applied as a liquid/gel to the skin surface which permits formation of an adherent film over any skin contour including elbows, knees, hips, and the like.

Since the polymeric film is naturally shed from the skin surface 2–4 days after application, there is no need to effect removal of the drape after surgery or to encounter the skin trauma potentially associated with drape removal. Moreover, in a preferred embodiment, the cyanoacrylate composition is formulated to contain an antimicrobial agent which will be released from the resulting film thereby providing for post-surgical infection protection not now available from conventional drapes.

Accordingly, in one of its method aspects, this invention is directed to a method for forming an adherent, surface conforming drape at a surgical incision site of a patient which method comprises:

(a) defining a surgical incision site on the patient;

(b) applying a sufficient amount of a cyanoacrylate composition onto the skin surface at the surgical incision site defined in (a) above so as to cover this site with the composition wherein the composition comprises a cyanoacrylate ester which, in monomeric form, is represented by formula I:

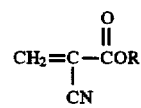

where R is selected from the group consisting of:
alkyl of 1 to 10 carbon atoms,
alkenyl of 2 to 10 carbon atoms,
cycloalkyl groups of from 5 to 8 carbon atoms,
phenyl,
2-ethoxyethyl,
3-methoxybutyl,
and a substituent of the formula:

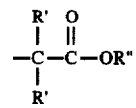

wherein each R' is independently selected from the group consisting of:
hydrogen and methyl, and
R" is selected from the group consisting of:
alkyl of from 1 to 6 carbon atoms,
alkenyl of from 2 to 6 carbon atoms,
alkynyl of from 2 to 6 carbon atoms,
cycloalkyl of from 3 to 8 carbon atoms,
aralkyl selected from the group consisting of benzyl, methylbenzyl and phenylethyl,
phenyl, and
phenyl substituted with 1 to 3 substituents selected from the group consisting of hydroxy, chloro, bromo, nitro, alkyl of 1 to 4 carbon atoms, and alkoxy of from 1 to 4 carbon atoms;

(c) polymerizing the cyanoacrylate so as to form a flexible, waterproof, adhesive polymer layer which adheres to the area(s) where the adhesive was applied; and (d) creating an incision through the polymer layer formed in (c) above.

Application of the layer of cyanoacrylate composition is preferably made onto the surface of intact skin and the incision is made subsequent to formation of the cyanoacrylate polymer layer. More preferably, the intact skin is further characterized as lacking any infection, open wounds, etc. which would permit the polymer to penetrate from the surface of the epidermis to or beyond the dermal layer.

Preferably, in the cyanoacrylate esters of formula I, R is alkyl of from 2 to 10 carbon atoms and more preferably alkyl of from 2 to 8 carbon atoms. Even more preferably, R is butyl, pentyl or octyl and most preferably, R is n-butyl.

In another preferred embodiment, the polymerized cyanoacrylate composition has a thickness of no more than about 1 millimeter and, more preferably, the polymer layer has a thickness of from about 2 to about 500 microns and still more preferably from about 20 to about 100 microns.

DETAILED DESCRIPTION OF THE PREFERRED EMBODIMENTS

This invention is directed to methods for draping a surgical incision site prior to surgery. However, prior to discussing this invention in further detail, the following terms will first be defined.

Definitions

As used herein, the following terms have the following meanings:

The term "surgical incision site" refers to the skin surface to which the surgical incision is to be made as well as the immediate area adjacent to the incision. This immediate area typically extends at least 1-2 inches in all directions beyond the incision and preferably extends by about 2 to 12 inches beyond the incision.

The term "incision" refers to any surgical penetration which extends beyond the dermal layer of the patient's skin and includes, by way of example, incisions made by needles, knives (including surgical knives and surgical cautery knives), trocars, etc.

The term "cyanoacrylate composition" or "cyanoacrylate adhesive composition" refers to polymerizable adhesive formulations comprising cyanoacrylate monomers or polymerizable oligomers which in their monomeric form are preferably compounds represented by formula I as described above.

More preferably, in formula I, R is an alkyl group of from 2 to 10 carbon atoms including ethyl, n-propyl, iso-propyl, n-butyl, iso-butyl, sec-butyl, n-pentyl, iso-pentyl, n-hexyl, iso-hexyl, 2-ethylhexyl, n-heptyl, octyl, nonyl, and decyl. More preferably, R is butyl, pentyl or octyl and most preferably, R is n-butyl.

These cyanoacrylates are known in the art and are described in, for example, U.S. Pat. Nos. 3,527,224; 3,591,676; 3,667,472; 3,995,641; 4,035,334; and 4,650,826 the disclosures of each are incorporated herein by reference in their entirety.

A preferred cyanoacrylate for use in the invention is n-butyl-2-cyanoacrylate.

The cyanoacrylate adhesive compositions described herein rapidly polymerize in the presence of water vapor or tissue protein, and the n-butyl-cyanoacrylate bonds human skin tissue without causing histotoxicity or cytotoxicity.

The term "biocompatible plasticizer" refers to any material which is soluble or dispersible in the cyanoacrylate composition, which increases the flexibility of the resulting polymer film coating on the skin surface, and which, in the amounts employed, is compatible with the skin as measured by the lack of skin irritation. Suitable plasticizers are well known in the art and include those disclosed in U.S. Pat. Nos. 2,784,127 and 4,444,933 the disclosures of both of which are incorporated herein by reference in their entirety. Specific plasticizers include, by way of example only, acetyl tri-n-butyl citrate (~20 weight percent or less), acetyl tri-hexyl titrate (~20 weight percent or less) butyl benzyl phthalate, dibutyl phthalate, dioctylphthalate, n-butyryl tri-n-hexyl citrate, diethylene glycol dibenzoate (~20 weight percent or less) and the like. The particular biocompatible plasticizer employed is not critical and preferred plasticizers include dioctylphthalate.

The term "surgical incision drape" refers to the drape formed over the surgical incision site and through which the surgical incision is made. The term surgical incision drape is synonymous with the term "incise drape" as used by Osuna, et al.[2]

The term "antimicrobial agent" refers to an agent which destroys microbes (i.e., bacteria, fungi, yeasts and viruses) thereby preventing their development and their pathogenic action.

Methods

The methods of this invention comprise the in situ formation of a cyanoacrylate polymer film on the skin surface at the surgical incision site of a patient which polymer film acts as a surgical incision drape.

The surgical protocol preferably involves skin preparation prior to in situ formation of the cyanoacrylate polymer drape over the surgical incision site. Specifically, an antimicrobial agent is applied to the cleaned surgical incision site. The antimicrobial agent can be any suitable agent including iodine based solutions, alcohols, etc. In one embodiment, an iodine prep solution is first applied to the surgical incision site. The patient's skin is then cleansed and scrubbed with this solution and subsequently washed off. Afterwards, an alcohol solution or a povodine iodine solution is applied to the surgical incision site to complete the skin preparation.

The surgical incision site is optionally dried and then an adherent polymeric drape is formed over this site by applying a cyanoacrylate adhesive composition to the intact skin surface at the surgical incision site. As noted above, this composition comprises polymerizable cyanoacrylate monomers and/or reactive oligomers which, upon contact with the surface skin moisture, tissue protein, etc. polymerizes in situ to form a cyanoacrylate polymer film.

Polymerization occurs at ambient skin temperature while maintaining the skin surface under suitable conditions to allow polymerization to proceed. In general, the particular length of time required for polymerization will vary depending on factors such as the amount of adhesive composition applied, the temperature of the skin, the moisture content of the skin, the surface area of skin to which the adhesive was applied, and the like. However, in a preferred embodiment, polymerization is generally complete within about 10 to about 60 seconds while the skin is maintained at ambient conditions. During this period, the patient is maintained in a position which permits the cyanoacrylate to polymerize and form a polymeric drape while minimizing any patient movement which might dislodge the cyanoacrylate from that surgical incision site.

Sufficient amounts of the adhesive composition are employed to cover (i.e., coat) the entire surgical incision site with a layer of the cyanoacrylate polymer. If necessary, excess cyanoacrylate monomer can be removed from the skin with a wipe or tissue before polymerization or, after polymerization, any polymer formed at unintended sites can be removed with acetone (nail polish remover).

After polymerization, the resulting polymeric film forms a surgical incise drape which strongly adheres to the skin, is flexible and waterproof. Such strong adherence effectively eliminates the possibility that the drape will lift away from the patient's skin during surgery. However, notwithstanding such strong adherence, the polymeric film defining the drape will only adhere to the skin for a period of about 2–4 days after which time it sloughs off. This occurs because the cyanoacrylate polymer adheres only to the uppermost portion of the epidermal layer which is continuously in the process of being sloughed off and replaced by the underlying cells. Accordingly, the cyanoacrylate drape need not be removed in the manner of conventional drapes whose removal can result in skin trauma.

The polymeric drape should be maintained in a unbroken manner over the entire surgical incision site. This can be assured by careful application of the cyanoacrylate adhesive onto the skin. Additionally, the use of a plasticizer will facilitate the maintenance of the polymeric drape in an unbroken manner and will inhibit cracking of the drape.

In one embodiment, after application of the initial polymeric layer, a second, preferably thinner, layer is applied thereto. Additional amounts of cyanoacrylate adhesive composition can be applied as needed to maintain an unbroken coating covering over the surface skin areas.

Application is conducted under conditions wherein the polymeric drape has a thickness of no more than about 1 millimeter and, more preferably, the polymer layer has a thickness of from about 2 to about 500 microns and still more preferably from about 20 to about 100 microns. If thinner polymeric drapes are desired, then the polymeric drape should have a thickness of from about 2 to about 50 microns and preferably from 10 to 40 microns. The amount of cyanoacrylate composition applied to a unit area of skin to obtain such thicknesses is well within the skill of the art.

Once the polymeric surgical incise drape is formed over the surgical incision site (which as defined above includes the areas adjacent to the incision itself), the polymeric surgical incise drape can then optionally be overdraped with sterile towels and sheets. In this optional embodiment, such towels and sheets are laid over (i.e., overdrape) the surgical incision drape to define a limited field of the surgical incise drape in which the actual incision is to be made and the subsequent operation is to be conducted.

In either case, the surgical incision is made through the polymeric surgical incise drape. Any conventional incision can be made including those created by needles, knives (including surgical knives and surgical cautery knives), trocar, and the like. The particular incision made is not critical and is, of course, made relative to the surgery to be conducted.

Once the incision is made, the surgery is conducted using conventional methods and, upon completion of the surgery, the surgical wound is closed by conventional methods. In one embodiment, however, closure of the dermal layer of the surgical wound can be accomplished by application of cyanoacrylate adhesive composition onto one or both of the opposing skin sections and maintaining contact between these skin sections until the cyanoacrylate has polymerized.

The size and thickness of the polymeric drape formed onto the skin surface area can be readily controlled by the amount and viscosity of cyanoacrylate adhesive composition packaged in a single dose product or by use of a multiple use dispenser which governs the amount of material applied onto a unit area of surface skin. In this regard, the dispenser described by Otake, U.S. Pat. No. 4,958,748, which is incorporated by reference in its entirety, is one example of a dispenser which dispenses the cyanoacrylate adhesive composition in a controlled dropwise manner. Other methods for the controlled dispersement of the cyanoacrylate adhesive include, by way of example, a spray applicator, brush, wipe, swab or solid paddle applicator, applicators for repeated and intermittent use of the cyanoacrylate composition and the like.

In applicators, the cyanoacrylate composition is stored at ambient conditions and can be sterilized as needed.

Because the cyanoacrylate polymer layer is waterproof, the patient is not prevented from bathing or being bathed and other activities involving exposure to water during the period the polymer layer protects the surgical incision site.

Compositions

The cyanoacrylate compositions described herein are prepared by conventional methods of mixing the appropriate components until homogenous.

The specific viscosity of these compositions depends, in part, on the intended application of the composition. For example, relatively low viscosities are often preferred where application is to be made to a large surface area (e.g., abdominal surfaces). This preference results from the fact that those forms are less viscous and, accordingly, will permit more facile large surface area application of a thin application. Contrarily, where application is to be made to a specific position on the skin (e.g., elbow surfaces), higher viscosity materials are preferred to prevent "running" of the material to unintended locations.

Accordingly, these compositions have a viscosity of from about 2 to 50,000 centipoise at 20° C. Preferably the less viscous compositions have a viscosity of from about 2 to 1,500 centipoise at 20° C. More preferably, the cyanoacrylate adhesive is almost entirely in monomeric form and the composition has a viscosity of from about 5 to about 500 centipoise at 20° C.

A thickening agent is optionally employed to increase the viscosity of the composition which thickening agent is any biocompatible material which increases the viscosity of the composition. Suitable thickening agents include, by way of example, polymethyl methacrylate (PMMA) or other preformed polymers soluble or dispersible in the composition, a suspending agent such as fumed silica and the like with PMMA being preferred. Fumed silica is particularly useful in producing a gel for topical application having a viscosity of from about 1500 to 50,000 centipoise at 20° C. Suitable thickening agents for the cyanoacrylate compositions described herein also include a partial polymer of the alkyl cyanoacrylate as disclosed in U.S. Pat. Nos. 3,654,239[8] and 4,038,345[15] both of which are incorporated herein by reference in their entirety.

Thickening agents are deemed to be biocompatible if they are soluble or dispersible in the composition and are compatible with the skin as measured by the lack of moderate to severe skin irritation.

The cyanoacrylate adhesive compositions preferably include a biocompatible plasticizer and such plasticizers are preferably included from about 10 to 30 weight percent and more preferably from about 18 to 25 weight percent based on the total weight of the composition absent any antimicrobial agent.

Additionally, the cyanoacrylate compositions described herein preferably include a polymerization inhibitor in an effective amount to inhibit premature polymerization of the composition. In a particularly preferred embodiment, this inhibitor is sulfur dioxide which is employed at from about 50 to 500 ppm based on the total weight of the composition absent any antimicrobial agent.

The cyanoacrylate adhesive compositions may additionally contain one or more optional additives such as colorants, perfumes, anti-diffusion agents, rubber modifiers, modifying agents, etc. In practice, each of these optional additives should be both miscible and compatible with the cyanoacrylate composition and the resulting polymer. Compatible additives are those that do not prevent the use of the cyanoacrylates in the manner described herein.

In general, colorants are added so that the polymer layer formed on the skin will contain a discrete and discernable color. Perfumes are added to provide a pleasant smell to the formulation. Rubber modifiers are added to further enhance the flexibility of the resulting polymer layer. The amount of each of these optional additives employed in the composition is an amount necessary to achieve the desired effect.

Preferred cyanoacrylate compositions useful in the practice of this invention are also disclosed by Greff, et al., U.S. Pat. No. 5,480,935, which patent is incorporated herein by reference in its entirety.

In a particularly preferred embodiment, the cyanoacrylate adhesive composition further comprises an antimicrobially effective amount of a compatible antimicrobial agent. Such compositions preferably comprise from about 1 to about 40 and preferably 5 to 30 weight percent of the compatible antimicrobial agent either as a solution or as a suspension based on the total weight of the composition. Compatible antimicrobial agents are those which are either soluble or suspendable in the cyanoacrylate composition, which do not cause premature polymerization or prevents polymerization of the cyanoacrylate composition when applied to mammalian skin, and which are compatible with the intended use including biocompatibility with the patient's skin.

In a particularly preferred embodiment, the compatible antimicrobial agent comprises a complex of iodine molecules with a biocompatible polymer. Such complexes are well known in the art and the resulting complex typically comprises both available iodine and iodide anions. These complexes, on contact with mammalian skin, provide for a source of antimicrobial iodine. In any event, such complexes are employed only as starting materials herein and, by themselves, do not form a part of this invention. Suitable biocompatible polymers include, by way of example only, polyvinylpyrrolidinone polymer which, when complexed with iodine, is also referred to under the common name of povidone-iodine available from BASF, Mt. Olive, N.J. USA. When povidone-iodine is employed in the cyanoacrylate composition, it is preferably from about 5 to about 40 weight percent and more preferably from about 10 to 25 weight percent is added to the cyanoacrylate composition based on the total weight of the composition.

Cyanoacrylate compositions comprising, for example, povidone-iodine are described by Greff, et al., U.S. patent application Ser. No. 08/781,409 U.S. Pat. No. 5,684,042 filed concurrently herewith as Attorney Docket No. 026446-066 and entitled "Cyanoacrylate Compositions Comprising an Antimicrobial Agent" which application is incorporated herein by reference in its entirety.

The use of a compatible antimicrobial agent in the composition permits the agent to be released from the polymeric drape thereby reducing microbial growth under the drape during surgery. Additionally, since the drape is maintained over the surgical incision site for 2–4 days after surgery, the release of antimicrobial agent further provides post-surgical anti-infection benefits.

Utility

The methods described herein are useful in forming a polymeric surgical incise drape over the surgical incision site of a mammalian patient. The polymeric drape finds particular utility in inhibiting microbial contamination of the incision during surgeries conducted on such patients. Such mammalian patients preferably include humans as well as domestic animals such as horses, cows, dogs, sheep, cats, etc. The maintenance of the polymeric film over the surgical incision after completion of the surgery is expected to reduce the incidence of infection by inhibiting microbial contamination of the incision.

The following examples illustrates certain embodiments of the invention but is not meant to limit the scope of the claims in any way.

EXAMPLE 1

This example illustrates how a surgical incise drape formed in the manner of this invention could be used during surgery. In this example, an abdominal surgical incision is to be made through a surgical incise drape of an adult human male and subsequent bladder surgery conducted through the incision.

Specifically, an adult human male (age 58) diagnosed with bladder cancer is scheduled for surgery. The patient (after thorough cleaning) is placed and secured on an operating table and anesthetized. Shaving of the surgical incision area can optionally be performed if such is deemed necessary by the attending surgeon. The patient then undergoes a five minute abdominal scrub using cleansing pads and an iodine based cleansing solution such as ethanolic povidone-iodine. After the surgical scrub, the abdomen is thoroughly rinsed with sterile distilled water. An antimicrobial solution of iodine is then applied to the same area and allowed to dry.

At this time, an antimicrobial cyanoacrylate composition comprising 73% by weight butyl cyanoacrylate, 17% by weight dioctylphthalate, 10% povidone iodine and 100 parts per million sulfur dioxide (each based on the total weight of the composition) is applied to an area of approximately 25 centimeters by 50 centimeters with the proposed incision site to be located in the center of this area. The composition is allowed to thoroughly cure (~60 seconds) whereupon a coherent, durable and flexible surgical incise drape is formed over the applied area. This area is then draped with standard sterile surgical drapes made of a waterproof paper material to create a surgical field within the surgical incise drape. The surgical field defines an area of approximately 10 centimeters by 20 centimeters at approximately the center of the surgical incise drape. An incision is then made through the surgical incise drape in this surgical field by a surgical knife and the bladder is removed uneventfully. Afterwards, the peritoneum, fascia and subcutaneous layers are closed with standard absorbable surgical sutures. The skin is then closed with a standard running skin suture.

At this time, the sterile surgical drapes made of a waterproof paper material are removed from the patient leaving only the surgical incise drape which is strongly adherent to the skin. A surgical dressing is applied over the incision site and the patient is awakened from the anesthetic agent. The surgical dressing is checked every 4 hours for signs of seepage and changed daily until patient is discharged (typically 2–3 days after surgery).

The surgical incise drape formed by the film of cyanoacrylate polymer sloughs off naturally over 2–4 days after surgery as the patient's outer layer of skin naturally sloughs off without any complications. The povidone-iodine in the film is antimicrobial thereby providing an antimicrobial effect during this period.

EXAMPLE 2

This example illustrates how a surgical incise drape formed in the manner of this invention could be used during arthroscopic surgery correcting a minor medial collateral ligament tear to a patient's knee. Because of the conformation of the knee, a higher viscosity cyanoacrylate composition is desirable in order to prevent "running" of the composition prior to formation of the polymeric drape. In this example, three separate surgical incisions are made with trocars through a polymeric surgical incise drape formed in the manner of this invention over the knee and subsequent repair of the torn ligaments is conducted through these trocars.

Specifically, an adult female (age 36) diagnosed with a torn medial collateral ligament of the right knee is scheduled for outpatient surgery to arthroscopically repair the torn ligaments. The patient, after thorough cleansing, is placed and secured on an operating table, and the leg is anesthetized. The patient then undergoes a five minute scrub of the knee using cleansing pads and an iodine based closing solution such as ethanolic povidone-iodine. After the surgical scrub, the knee is thoroughly rinsed with sterile distilled water. An atimicrobial solution of iodine is then applied to the same area and allowed to dry.

At this time, a viscous antimicrobial cyanoacrylate composition comprising 68% by weight butyl cyanoacrylate, 5 weight percent polymethyl methacrylate, 17% by weight dioctylphthalate,. 10% povidone iodine and 100 parts per million sulfur dioxide (each based on the total weight of the composition) is applied to the entire knee area extending approximately 5 centimeters above and below the knee joint with the proposed trocar incision sites to be located within the boundaries of this area. The composition is allowed to thoroughly cure (~60 seconds) whereupon a coherent, durable and flexible surgical incise drape is formed over the applied area. This area is then draped with standard sterile surgical drapes made of a waterproof paper material to create a surgical field within the surgical incise drape. Three separate incisions are made into the knee joint through the surgical incise drape in this surgical field by three separate trocars and the medial collateral ligament tear is repaired uneventfully. Afterwards, the skin is closed with a separate cyanoacrylate composition that bonds the skin edges together and holds them until the wound heals itself. The cyanoacrylate polymeric film naturally sloughs off within 2–4 days after formation. The povidone-iodine in the film renders the film antimicrobial thereby providing an antimicrobial effect during this period.

From the foregoing description, various modifications and changes in the composition and method will occur to those skilled in the art. All such modifications coming within the scope of the appended claims are intended to be included therein.

What is claimed is:

1. A method for forming an adherent, surface conforming drape at a surgical incision site of a patient which method comprises:

(a) defining a surgical incision site on the patient;

(b) applying a sufficient amount of a cyanoacrylate composition comprising a polymerizable cyanoacrylate ester monomer or oligomer onto the skin surface of the patient at the surgical incision site defined in (a) above so as to cover this site with the cyanoacrylate composition;

(c) polymerizing the cyanoacrylate ester so as to form a flexible, waterproof, adhesive polymer layer which adheres to the area(s) where the cyanoacrylate ester was applied; and (d) creating an incision through the polymer layer formed in (c) above.

2. The method according to claim 1 wherein the polymerizable cyanoacrylate composition comprises a cyanoacrylate ester which, in monomeric form, is represented by Formula I:

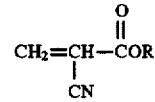

wherein R is selected from the group consisting of:
alkyl of from 1 to 10 carbon atoms,
alkenyl of 2 to 10 carbon atoms,
cycloalkyl of from 5 to 8 carbon atoms,
phenyl,
2-ethoxyethyl,
3-methoxybutyl,
and a substituent of the formula

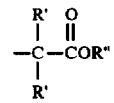

wherein each R' is independently selected from the group consisting of: hydrogen and methyl, and
R" is selected from the group consisting of:
alkyl of from 1 to 6 carbon atoms;
alkenyl of from 2 to 6 carbon atoms;
alkynyl of from 2 to 6 carbon atoms;
cycloalkyl of from 3 to 8 carbon atoms;
aralkyl selected from the group consisting of benzyl, methylbenzyl and phenylethyl,
phenyl,
phenyl substituted with 1 to 3 substituents selected from the group consisting of hydroxyl, chloro, bromo, nitro, alkyl of 1 to 4 carbon atoms, and alkoxy of from 1 to 4 carbon atoms.

3. The method according to claim 2 wherein R is alkyl of from 2 to 8 carbon atoms.

4. The method according to claim 3 wherein R is selected from the group consisting of butyl, pentyl or octyl.

5. The method according to claim 4 wherein R is n-butyl.

6. The method according to claim 1 wherein said cyanoacrylate composition further comprises an antimicrobially effective amount of a compatible antimicrobial agent.

7. The method according to claim 6 wherein the compatible antimicrobial agent is polyvinylpyrrolidone iodine.

8. The method according to claim 1 wherein said cyanoacrylate composition further comprises a biocompatible plasticizer.

9. The method according to claim 8 wherein said biocompatible plasticizer is dioctyl phthalate.

10. The method according to claim 1 wherein said cyanoacrylate composition further comprises a polymerization inhibitor.

11. The method according to claim 10 wherein said polymerization inhibitor is $SO_2$.

12. The method according to claim 1 wherein the polymer layer has a thickness of no more than about 1 millimeter.

13. The method according to claim 1 which further comprises closing the dermal layer of the surgical incision with a polymerizable cyanoacrylate composition comprising a polymerizable cyanoacrylate ester monomer or oligomer.

14. A method for forming an adherent, surface conforming drape at a surgical incision site of a patient which method comprises:

(a) defining a surgical incision site on the patient;

(b) applying a sufficient amount of a cyanoacrylate composition comprising a polymerizable cyanoacrylate ester monomer or oligomer onto the skin surface of the patient at the surgical incision site defined in (a) above so as to cover this site with the cyanoacrylate composition wherein the cyanoacrylate composition comprises:

(i) polymerizable n-butyl cyanoacrylate which, in monomeric form, is represented by formula II:

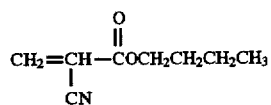

(ii) from about 18 to 25 weight percent of dioctylphthalate based on the total weight of the composition absent polyvinylpyrrolidone iodine;

(iii) from about 50 to about 500 ppm sulfur dioxide based on the total weight of the composition absent polyvinylpyrrolidone iodine;

(iv) from 5 to 40 weight percent of polyvinylpyrrolidone iodine based on the total weight of the composition;

(c) polymerizing the cyanoacrylate ester so as to form a flexible, waterproof, polymer layer which adheres to the area(s) where the cyanoacrylate composition was applied; and (d) creating an incision through the polymer layer formed in (c) above.

* * * * *